US005563043A

United States Patent [19]
Schalkowsky et al.

[11] Patent Number: 5,563,043
[45] Date of Patent: Oct. 8, 1996

[54] METHOD FOR MEASURING THE BACTERICIDAL AND BACTERIOSTATIC EFFECTS OF ANTIMICROBIAL AGENTS

[75] Inventors: Samuel Schalkowsky, Chevy Chase, Md.; Leon G. Hunt, Arlington, Va.

[73] Assignee: Spiral Biotech, Inc., Bethesda, Md.

[21] Appl. No.: 328,160

[22] Filed: Oct. 24, 1994

[51] Int. Cl.$^6$ ................... C12Q 1/18; C12Q 1/02
[52] U.S. Cl. ................... 435/32; 435/29; 435/39
[58] Field of Search ................... 435/29, 30, 32, 435/39

[56] References Cited

U.S. PATENT DOCUMENTS

| | | | |
|---|---|---|---|
| 4,101,383 | 7/1978 | Wyatt | 195/103.5 R |
| 4,514,495 | 4/1985 | Schalkowsky | 435/32 |
| 4,517,292 | 5/1985 | Schalkowsky | 435/32 |
| 4,637,053 | 1/1987 | Schalkowsky | 382/6 |
| 5,246,837 | 9/1993 | Schalkowsky | 435/29 |

OTHER PUBLICATIONS

Garrett E., Kinetics Of Antimicrobial Action Scand J Infect Dis Suppl 14: 54–85 1978.
"Measures of Susceptibility From a Spiral Gradient of Drug Concentrations" appearing in *Antimicrobial Susceptibility Testing: Critical Issues of the 90's* (Poupard et al. Ed.), pp. 107–120, Plenum Press, New York 1994.
NCCLS (Nat'l. Committee for Clinical Laboratory Standards) (1990a). *Methods for Antimicrobial Susceptibility Testing of Anaerobic Bacteria—Second Edition; Approved Standard M11–A2*. NCCLS, Villanova PA; NCCLS (Nat'l Committee for Clinical Laboratory Standards) (1990b). *Methods for Dilution Antimicrobial Susceptibility Tests for Bacteria that Grow Aerobically—Second Edition; Approved Standard M7–A2*. NCCLS, Villanova PA.
Journal of Antimicrobial Chemotherapy 27, Suppl. D. 1991.
Tentative Guideline, NCCLS Document M26–T, vol. 12, No. 19 (Sep. 1992) entitled "Methods for Determining Bactericidal Activity of Antimicrobial Agents".
Proposed Guideline, NCCLS Document M26–P, vol. 7, No. 2 (Sep. 1986), NCCLS, Villanova, Pa.
Journal of General Microbiology (1986) 132, pp. 1297–1304, entitled "The Rate of Killing of *Excherichia coli* by β–Lactam Antibiotics Is Strictly Proportional to the Rate of Bacterial Growth", by E. Tuomanen, R. Cozens, W. Tosch, O. Zak and A. Tomasz.

*Primary Examiner*—Ralph J. Gitomer
*Attorney, Agent, or Firm*—Antonelli, Terry, Stout & Kraus

[57] ABSTRACT

A method for measuring the combined bactericidal and bacteriostatic effects of an antimicrobial agent on the number of viable cells in a bacterial population exposed to an application-relevant concentration of the agent, with the rate of change of the number of viable cells as a function of different exposure intervals expressed on a per-drug-free division interval $g_0$ (generation time) basis, so as to facilitate the assessment of projected therapeutic efficacy independent of the particular generation time used in the test environment. (2) A method for measuring the combined bactericidal and bacteriostatic effects of an antimicrobial agent on the acceleration of viable population change at a concentration corresponding to the Discrete Minimal Inhibitory Concentration (DMIC), when the size of the initial viable population remains essentially unchanged in the presence of the agent. (3) A method for measuring the bactericidal component of the effect of an antimicrobial agent from measurements of the initial viable population deposited on nutrient agar media and the number of visible colonies which formed from this deposit in the presence of a selected concentration of the antimicrobial agent. (4) A method for determining the value of the DMIC, and the rate of change of bactericidal activity with changing concentrations of the antimicrobial agent, by applying the method of (3) above at different concentrations of the antimicrobial agent; computing the probability of successful cell division from colony count data at the selected concentrations of the antimicrobial agent; evaluating the functional relationship between the probabilities of division and concentration of the agent; and obtaining from this function the value of the DMIC, the Minimum Cidal Concentration (MCC) where bactericidal activity begins and the rate of change of bactericidal activity with drug concentration.

20 Claims, 4 Drawing Sheets

METHOD FOR MEASURING THE BACTERICIDAL AND BACTERIOSTATIC EFFECTS OF ANTIMICROBIAL AGENTS

TECHNICAL FIELD

The invention relates to methods for measuring growth rates of bacterial populations subject to bactericidal (killing) and bacteriostatic (reproduction rate) actions of antimicrobial agents.

Typical antimicrobial agents are (1) antibiotics (drugs) used to reduce the size or to eradicate pathogenic microbial populations in clinical treatment, (2) decontaminants used in hygiene control applications, (3) preservatives (biocides) used to control the growth or to eradicate contaminating bacteria of cosmetic products, and (4) heat, radiation or other antimicrobial environments used to homogenize or sterilize food products.

BACKGROUND ART

The current art of measuring antimicrobial efficacy does not take into account concurrent bactericidal and bacteriostatic activity. It also lacks a unifying structure for the integration of observed responses of a bacterial population to the action of an antimicrobial agent. As a result, test methods are currently based on the nature of the observation unique to the particular test, viz. the absence of visible colonies or turbidity, rather than on independent criteria of efficacy which the test would seek to measure. The relationship between test measurements and the purpose of the test are therefore elusive; even those highly skilled in the art are unable to select test procedures and to define associated protocols which can reliably relate test measurements to therapeutic efficacy criteria. Thus, the prior art, while rich in knowledge concerning effects at the level of the individual cell, suffers from the fundamental deficiency of lacking a practical, theoretical basis for relating the response of a bacterial population to the bactericidal and bacteriostatic actions of an antimicrobial agent.

Inadequacies of the prior art as it applies to the testing of antimicrobial agents in clinical practice and new drug development are summarized below.

The most common measurement characterizing the effect of an antimicrobial agent, and providing a basis for assessing its potential efficacy to combat pathogens, is the Minimum Inhibitory Concentration (MIC): it is the concentration of the agent—generally in a series of twofold dilutions—which leads to suppression of growth as observed in the test. By currently accepted standards as published in the following publications: (1) NCCLS (National Committee for Clinical Laboratory Standards) (1990a). *Methods for Antimicrobial Susceptibility Testing of Anaerobic Bacteria—Second Edition; Approved Standard* M11-A2. NCCLS, Villanova Pa.; NCCLS (National Committee for Clinical Laboratory Standards) (1990b) and (2) *Methods for Dilution Antimicrobial Susceptibility Tests for Bacteria that Grow Aerobically—Second Edition; Approved Standard* M7-A2. NCCLS, Villanova Pa., the MIC cannot be defined as an absolute quantity and a wide tolerance of +/− one twofold dilution—a range of 300 percent—is accepted as the practically achievable accuracy of its measurement. Observation of growth transition features—from contiguous growth of colonies to their complete absence on agar media, or partial turbidity in broth dilution tests—are neglected, or subject to diverse interpretations, because their source and relevance are not understood (they also contribute to the wide variation of test results). It is therefore not surprising that the specification of MIC breakpoint values, used to judge whether a bacterial isolate will be susceptible or resistant to treatment by the tested antimicrobial agent, is subject to considerable uncertainty. Indeed, the Working Party of the British Society for Antimicrobial Chemotherapy states in the introduction to their Guide to Sensitivity Testing that "the only clear property of breakpoint antibiotic concentrations is that they are largely arbitrary" (Journal of Antimicrobial Chemotherapy 27, Suppl. D, 1991).

In a presentation to a symposium of the American Society of Microbiology in Philadelphia, Pa., November, 1991, Samuel Schalkowsky defined the MIC as a discrete quantity on a continuous scale of concentrations of the antimicrobial agent, referred to as the Discrete MIC (DMIC). See Schalkowsky, S. (1991) Measures of Susceptibility from a Spiral Gradient of Drug Concentrations. In *Antimicrobial Susceptibility Testing: Critical Issues of the 90's* (Poupard et al. Ed.) pp 107–120, Plenum Press, New York 1994. Specifically, the DMIC represents the concentration of the antimicrobial agent resulting in essentially no change from the initial number of viable cells in the test population with increasing time of exposure to the drug. Reductions in the viable population will be exhibited at higher concentrations while increasing populations will result at concentrations lower than the DMIC. Schalkowsky proposed that the DMIC be measured by means of time-kill curves at concentrations near the DMIC, by obtaining their slopes for short exposure intervals, performing a regression of these slopes against their corresponding drug concentrations, and obtaining the DMIC value as the concentration at which the regression line intercepts the concentration axis, i.e. when the slope is equal to zero. Thus, the DMIC was defined by the horizontal time-exposure axis of conventional time-kill curves.

The need to assess the bactericidal activity of antimicrobial agents is well recognized. The most common estimator of bactericidal activity is the Minimal Bactericidal Concentration (MBC). It is the twofold dilution of the antimicrobial agent which reduces the original viable bacterial population by at least a factor of 1,000 (99.9%) after exposure for a (arbitrarily) preselected period of time, e.g. 24 hours. Current practice and problems associated with the MBC are documented by a subcommittee of the National Committee for Clinical Laboratory Standards (NCCLS) charged with the formulation of standardized laboratory methods for the testing of bactericidal activity. In September 1992 the NCCLS published Document M26-T as a Tentative Guideline of "Methods for Determining Bactericidal Activity of Antimicrobial Agents". This document (M26-T) follows the earlier issuance in 1986 of the Proposed Guideline, M26-P. See NCCLS (National Committee for Clinical Laboratory Standards) (1986). *Methods for Determining Bactericidal Activity of Antimicrobial Agents*; Proposed Guideline M26-P. NCCLS, Villanova Pa. The Tentative Guideline incorporates modifications resulting from comments received in the intervening six years in response to the Proposed Guideline, as a part of the consensus development process. The NCCLS document M26-T is therefore a highly authoritative representation of the current art of bactericidal activity testing and it clearly states that "The determination of the MBC . . . is so subject to methodologic variables that the clinical relevance of MBCs is nearly impossible to assess." Thus, again, in the prior art the relationship between test measurements and the objective of assessing the practical relevance of the test is elusive, at best.

NCCLS M26-T identifies specific problems causing uncertainty in the interpretation of bactericidal activity measurement. The four listed "biological factors" are (1) persisters, (2) paradoxical effect, (3) tolerance and (4) phenotypic resistance.

The expressing of the rate of population change on a per drug-free generation has been used by Tuomanen et al. to report results of laboratory tests dealing with the "rate of killing" of the tested antimicrobial agent. See Tuomanen, E., Cozens, R., Tosch, W., Zak, O. & Thomasz, A. (1986); the rate of killing of *Escherichia coli* by β-lactam antibiotics is strictly proportional to the rate of bacterial growth. *Journal of General Microbiology* 132, 1297–1304. This Tuomanen et al. reference is cited and its conclusion paraphrased in the NCCLS M26-T document as part of the attempt to describe the above persisters factor. It did not serve to define a useful measurement of antimicrobial efficacy.

In the prior art, the MIC is frequently referred to as a measure of bacteriostatic activity. But this is a convention rather than a scientifically established fact (it has likely evolved as a result of the existence of the separate MBC measurement which refers to bactericidal activity).

In the current art assessment of the efficacy of drug combinations are made using the imprecise, twofold MIC techniques, seeking to determine the elusive "synergistic" property of a combination, i.e. whether 1 plus 1 equals 3.

DISCLOSURE OF INVENTION

Probability Model of Antimicrobial Action

The methods defined by this invention derive from a probability model, developed by the inventors, of the interaction between an antimicrobial agent and a bacterial population which explicitly defines the effect of concurrent or separate bactericidal and bacteriostatic actions of the agent on the rates of change of the number of viable cells in the bacterial population (the model). The probability model leads to the formulation of meaningful criteria of efficacy, methods for measuring the degree to which they are achieved, and a way to relate them to each other.

The bacteriostatic effect is defined in terms of the probabilities of the cells in the population successfully dividing in a particular time interval. Bacteriostatic action is defined as a change in the probability distribution of the interdivision intervals. Bactericidal action is defined in terms of the probability, q, that any one cell in the population will be killed (rendered incapable of further division) in the presence of the drug (antimicrobial agent), in the course of the interdivision time-interval which would otherwise result in two viable cells. In the general model, this probability is also represented by a frequency distribution, which will vary with drug concentration.

The uncertainty in the interpretation of bactericidal activity measurement caused by (1) persisters, (2) paradoxical effect, (3) tolerance and (4) phenotypic resistance is addressed and resolved by the probability model of the present invention. Of the six "technical factors" listed in NCCLS M26-T, the two principal ones, viz. growth phase of inoculum and inoculum size (commonly referred to as the inoculum effect), are also addressed by the probability model of the present invention. The additional listed technical factors of insufficient contact, volume transferred, antibiotic carryover and choice of media relate to laboratory practice. The above problems of the prior art are integrated into the structure of the probability model of the present invention, preventing their obstructing the quantitative assessment of the relationship between a particular test measurement and the potential of the antimicrobial agent in reducing or eradicating the bacterial population.

The model leads to the formulation of a "normalized activity" measurement as the rate of change of the viable population per antimicrobial agent-free generation. Normalized activity aims to assess the combined bactericidal and bacteriostatic effect at any concentration of the antimicrobial agent. Of particular interest are antimicrobial agent concentrations expected to be achieved in vivo at the suspected site of infection. This formulation of normalized activity is derived from the model.

Even though Tuomanen et al. also expressed the rate of population change on a per drug free generation, a useful basis for the measurement of antimicrobial efficacy required the development of the probability model of the present invention and its application to define normalized activity in terms of the number of antimicrobial agent-free generations which will achieve a desired reduction of the target bacterial population due to the bactericidal as well as bacteriostatic activity of the antimicrobial agent.

The general probability model of antimicrobial action is simplified for the purposes of the present invention by replacing probability frequency distributions with fixed probability values, applicable to all members of the population at a constant concentration of the antimicrobial agent. The population is considered to be homogeneous in this respect, with the fixed probability values representing the modes of the frequency distributions. Thus, in the absence of antimicrobial agent activity, all cells in the population are taken to have the same interdivision time intervals (generation time), $g_0$. A different, but also fixed generation time, g, will be the result of bacteriostatic action, such that $g = k \times g_0$. The proportionality constant, k, is assumed to be the same for all the members of a homogeneous bacterial population and independent of the particular value of $g_0$.

The characterization of the MIC as a measure of bacteriostatic activity is shown to be erroneous by the probability model. Specifically, the model highlights the fact that bactericidal and bacteriostatic activity are not mutually exclusive but can act simultaneously to produce responses which, in the prior art, are characterized as "problems". Furthermore, the model shows that, while the antimicrobial agent can exert bacteriostatic as well as bactericidal action at the DMIC, the DMIC measurement itself reflects only the bactericidal—not the bacteriostatic—activity at this unique concentration. These insights led to the formulation of the test methods of this invention which specifically seek (1) to measure the relative bactericidal/bacteriostatic activity of the antimicrobial agent at the DMIC (extinction potential), (2) to separately measure its bactericidal component (bactericidal dose-response), and (3) by removing the results of (2) from (1), to determine the bacteriostatic component at the DMIC.

The direct, quantitative link between laboratory test results and application efficacy provided by the embodiments of this invention is of particular relevance to the assessment of the efficacy of antimicrobial agent combinations in clinical therapy, which has become highly relevant because of the increasing frequency and extent of pathogens becoming resistant to the action of available individual antibiotics.

The methods of this invention can address the question of synergy in an unequivocal manner: they provide a quantitative answer to the question whether the use of a particular antimicrobial agent combination will provide the needed reduction or eradication of the pathogenic bacterial population.

The probability model of the present invention provides a theoretical basis for the observed variation of (phenotypic) resistance amongst members of a bacterial population. It also explains the frequently reported "inoculum effect", when the observed test result is affected by changing the density of cells in the test population: it is due to the inclusion of more cells from the tails of the distributions at the higher cell densities.

For bactericidal action, rather than using a kill probability q, it is more convenient to deal with the complementary probability, p=1−q, that a cell will successfully divide in the presence of the antimicrobial agent. In the homogeneous population model of the present invention, the division probability, p, is the same for all cells in the population at a constant antimicrobial agent concentration; it defines the fraction of the initial viable population which will, on the average, successfully divide into two cells by the end of the division interval. Thus, if p=0.4 and 100 cells where initially viable, there will be 80 live cells at the end of the division interval (0.4×100×2).

Normalized Activity

For the simplified, homogeneous population model, both p and $g_0/g$ are the same for all the cells in the population at a constant concentration of the antimicrobial agent. For an initial population of live cells, Ni, the average number of live cells after the first division will be Ni×2×p. After two divisions it will be Ni×2p×2p. After n divisions the number of live cells, N(n), will be:

$$N(n)=Ni\times(2p)^n \quad (Eq. 1)$$

Note that when p=1, i.e. in the absence of the antimicrobial agent, the population doubles each division.

The actual number of generations, n, is not known when $g_0 \neq g$. Replacing n by $(g_0/g)\times n_0$, where $n_0$ is the equivalent number of antimicrobial agent-free generations, and taking logarithms to the base 2, equation 1 becomes:

$$\ln_2(N(n)/Ni)=\ln_2(N/N_i)=[\ln_2(2p)\times(g_0/g)]\times n_0 \quad (Eq. 2)$$

where N is the ending and $N_i$ is the starting viable cell number expressed on a per unit volume basis.

Equation 2 defines a normalized kill curve: it is a straight line of binary population reduction, $\ln_2(N/N_i)$, as a function of normalized time expressed in units of antimicrobial agent-free generations, $n_0$. The slope—defined by the expression in the square brackets—represents the product of bactericidal activity, $\ln_2(2p)$, and bacteriostatic activity, $g_0/g$. This slope is the quantity to be measured. It is referred to as normalized activity, or activity, A, and is given by $A=\ln_2(N/N_i)/n_0$. Hence, $$A=\ln_2(2p)\times(g_0/g) \quad (Eq. 2a)$$

Note that activity of the antimicrobial agent, as defined by the model of the present invention, allows for simultaneous bactericidal and bacteriostatic action, i.e. they are not mutually exclusive. Since bacteriostatic action decreases the value of $g_0/g$, it serves to reduce the effect of $\ln_2(2p)$ and will be referred to as static attenuation of the cidal activity.

Experimental data published by Tuomanen et al. (1986) corroborates the validity of equation 2, showing that at a constant concentration of the antimicrobial agent but at different antimicrobial agent-free generation times of a bacterial population achieved in a chemostat, the rate of population reduction is essentially the same when the logarithm of the survivor population is plotted against exposure time expressed in numbers of drug-free generations. This is predicted by equation 2 either when there is no bacteriostatic activity ($g_0 \neq g$), or if the ratio of $g_0/g$ remains the same even though $g_0$ changes. (In the Tuomanen et al. experiments $g_0$ ranged from 1.5 to 12.6 hours.)

The paradoxical effect is the result of static attenuation overcoming bactericidal action with increasing antimicrobial agent-free concentrations: activity increases initially, but at a decreasing rate, reaches a maximum value and then decreases.

Contrary to traditional reference to the MIC as a bacteriostatic measurement, the DMIC is a measure of bactericidal activity since it is obtained only when $\ln_2(2p)=0$ in equation 2 because p=0.5. (The case of an infinite value of g, which yields the same result, is not of practical significance.)

Normalized activity becomes a direct, quantitative measure of drug combination efficacy. Synergy/antagonism are evaluated quantitatively by observing whether the measured activity of the combination is greater or smaller than the sum of the activities of the individual antimicrobial agents when tested alone. To be consistent with the assumptions of the homogeneous population model of the present invention, the experimental procedure should be guided by the following:

(1) The initial test population should have the smallest number of cells needed to achieve acceptable measurement sensitivity. This will minimize the presence of cells from the tails of the distribution of interdivision times or cidal probabilities, i.e. it will minimize the expression of "phenotypic resistance".

(2) The culture should be at the beginning of the log phase when the antimicrobial agent is applied to it. At this point in time the population will consist predominantly of cells dividing in time intervals near the mode (peak) of the frequency distribution, which is the value represented by the model of the present invention.

(3) Exposure time to the antimicrobial agent should be limited to a few antimicrobial agent-free generations, because cells from the tail of the distribution of interdivision times become a more significant part of the total as the number of divisions increases.

While normalized activity is a quantitative measure of population change, e.g. A=−1 represents a twofold reduction in the population per antimicrobial agent-free generation, it may be more convenient to express the result as the number of antimicrobial agent-free generations (DFGs) needed to achieve a desirable reduction. Thus, for 10 DFGs ($n_0=10$), an activity of A=−1 implies a survivor fraction of about 1 in a thousand (for $\ln_2(N/N_i)=-10$, $N/N_i \neq 0.001$), i.e. 99.9% are killed. Denoting the time period needed to achieve such a 99.9% change in the population as the Bactericidal Reduction Period (BRP), then $$BRP=-(10/A)\ DFGs \quad (Eq. 3)$$

Note the critical requirement to express elapsed time in antimicrobial agent-free generations. For, by doing so, a result obtained in the laboratory with relatively short generation times can then be applied to the clinical situation involving different antimicrobial agent-free generation times. Thus, slowly growing pathogens will require a longer elapsed time to achieve the desired population reduction in vivo, but in the same, predicted number of drug-free generations.

Consensus-based values of the BRP can serve as interpretive standards of efficacy.

Definition of the Discrete MIC (DMIC)

As previously noted, the DMIC has been defined as a discrete quantity on a continuous scale of concentrations of the antimicrobial agent. (See Schalkowsky, S. (1991). Measures of Susceptibility form a Spiral Gradient of Drug concentrations. In *Antimicrobial Susceptibility Testing: Critical Issues of the 90's* (Poupard et al. ED.) pp 107–120, Plenum Press, New York 1994), the DMIC can be defined by reference to conventional time-kill curves. In terms of the probability model, the DMIC becomes the concentration for which the probability of division is p=0.5. Thus, at the DMIC there is a 50—50 probability of a cell successfully dividing or being killed. The total number of viable cells therefore remains constant, because, on the average, half the population is killed but the other half doubles. For p>0.5 the population will increase with each division, representing the restrained growth region. For p<0.5 the viable population will decrease with each division, since more cells are killed than successfully divide.

Population Transition Measures

The value of the DMIC is of interest as an indicator of the transition from restrained growth to population reduction. However, to be meaningful, it must be complemented by information on the rate of change of activity at the DMIC—the Transition Activity Rate (TAR)—because it is indicative of the rapidity of population eradication at the clinically more relevant concentrations above the DMIC.

The TAR is obtained from the same data used to compute the DMIC. Thus, while the DMIC is obtained from the intersection of the regression line of activity (slopes) versus concentration, the TAR is given by the slope of the regression line with the antimicrobial agent concentration axis.

The TAR describes the acceleration of population change at the DMIC. Its value is determined by the combined bactericidal as well as bacteriostatic activity of the antimicrobial agent: the steeper the slope of the DMIC regression line, the greater the bactericidal activity and the more rapid the eradication of the bacterial population. A shallow slope is indicative of tolerance.

The TAR may be particularly useful in attempting to quantitate the relative bacteriostatic/bactericidal activity of a particular isolate/antimicrobial interaction. However, to compare transition activity rates of different isolate/antimicrobial agent combinations it is necessary to normalize the antimicrobial agent concentration so as to make the measured activity rates independent of the particular value of the DMIC of the combination. This is done by rescaling the concentration axis to express it in multiples of the DMIC, denoted as XDMIC. A regression of the transformed data will yield the value of the slope of the regression line, which—to differentiate it from the TAR—is referred to as the Extinction Index (EI).

Bactericidal Activity Measures

Although both bacteriostatic as well bactericidal action may be exerted concurrently by the antimicrobial agent, the bactericidal component—represented by the probability of division, p—can be determined from the observation of the number of colonies which form on agar in the presence of the antimicrobial agent. The effect of bacteriostatic action can be largely excluded, provided incubation is sufficiently long for colonies to become visible, since the principal effect of bacteriostatic action is on the rate of colony growth rather than on the fraction of the initial cell deposit which will form colonies. The value of p is obtained from the fraction Nc/Ni, where Nc is the number of visible colonies which have formed on the surface of a nutrient agar plate while incubating in the presence of the antimicrobial agent which had been incorporated into the agar medium at a selected concentration, CNC, and Ni is the number of cells initially deposited onto the surface of the agar. The relationship between p and Nc/Ni stems from the following.

The steady-state extinction probability, Q, defines the fraction of the deposited cells that will not form visible colonies, when the probability of any one cell dividing successfully in the presence of the drug is p. "Steady-state" for purposes of the invention is a sufficiently long incubation period so that a large number of divisions will have occurred for the population within a colony to have been killed off or for a colony to become visible due to the accumulation of live and dead cells. Of principal interest is the complementary probability P=1−Q, as it represents the fraction of the deposited cells, Ni, that will form Nc visible colonies, i.e. P is the steady-state fraction of visible colonies from an initial population of Ni cells.

Q may be derived as follows. Starting with one bacterium, after division the probability distribution for the size of the first generation, $G_1$, is p for $G_1$=2 and q for $G_1$=0. The probability generating function for the size of the first generation is therefore:

$$P_1(s) = a_0 + a_1 \times s + a_2 \times s^2 + \ldots = q + p \times s^2$$

By definition, the generating function for the size of the nth generation of a branching process of this type is a composite function of the preceding generation's function, i.e., $$P_n(s) = P[P_{n-1}(s)]$$

The extinction probability $Q_n$, the probability that there are no living bacteria in the nth generation, is therefore:

$$Q_n = P_n(s) = P[P_{n-1}(s)]$$

for s=0
so that $$Q_1 = q$$
$$Q_2 = q + p \times q^2$$
$$Q_3 = q + p \times (q + p \times q^2)^2 \quad = \quad q + p \times P_2(s)^2, s = 0$$
$$\phantom{Q_3 = q + p \times (q + p \times q^2)^2} \quad = \quad q + p \times Q_2^2$$

and so on.

At steady state (as n approaches infinity), $Q_n = Q_{n-1}$. Therefore, by induction, $$Q_n = q + p \times Q_{n-1}^2 = q + p \times Q^2$$

provided p is greater than 0.5, applicable to the restrained growth region. (For values of p<0.5 the steady-state extinction probability is always 1.)

The above equation can be rewritten as $$(Q-1) = p \times (Q^2 - 1) = p \times (Q-1) \times (Q+1)$$

which simplifies to Q=(1−p)/p

Since we are interested in $(Nc/Ni)_{ss}$, and since P=1−Q, $$(Nc/Ni)_{ss} = 2 - 1/p$$

for $$0.5 < p \leq 1$$

which, omitting the ss subscript, is readily rearranged as $$p = 1/[2-(Nc/Ni)] \quad \text{(Eq. 4a)}$$

The Cidal Activity component (CA), defined in equation 2 as $\ln_2(2p)$, becomes $$CA = \ln_2(2p) = -\ln_2[1 - 0.5 \times Nc/Ni] \quad \text{(Eq. 4b)}$$

Although visible colonies will only form in the restrained growth (subinhibitory) region of p>0.5, the colony count at different antimicrobial agent concentrations for which p<1 can be used to determine the DMIC and the Transition Cidal Activity Rate (TCAR).

Bactericidal activity measures are obtained from a linear regression of a set of measurements for which p is less than 1. A function of concentration, f(CNC) is selected by conventional data analysis techniques to produce a linear relationship against $\ln_2(2p)$. The DMIC is obtained by setting p=0.5 in the equation of the regression line. The Minimum Cidal Concentration (MCC), the concentration at which cidal activity begins, is obtained by setting p=1 in the equation of the regression line. Of particular interest is the slope of this regression line, as it quantitates the Transition Cidal Activity Rate. Knowing this component of the rate of change of activity at the DMIC, as well as the previously defined combined cidal and static activity rates at the DMIC, the TAR, it is possible to obtain the Transition Static Activity, $TSA = (g_0/g)_{DMIC}$, from:

$$TSA = TAR/TCAR \quad \text{(Eq. 5)}$$

For values of p<0.5, i.e. in the population reduction region, cells may initially replicate, but the population will become extinct after a number of divisions. However, if the rate of division is small because of extensive static attenuation—which is the case for tolerance—"persister" cells may be found on agar at concentrations above the DMIC after the antimicrobial agent has been inactivated following standard incubation times.

A method for determining simultaneous bactericidal and bacteriostatic activity of an antimicrobial agent by measuring a time rate of change, expressed as A, of a function f(N) having a number of viable cells, expressed as N, in a microbial population with time of exposure to a selected concentration of an antimicrobial agent with the function f(N) being linearly related to a normalized exposure time expressed as a number $n_0$ of division time intervals $g_0$ representing a generation time of the microbial population in an absence of any antimicrobial agent in accordance with the invention includes determining by measurement $g_0$ of the microbial population; exposing a test culture of the microbial population containing a number Ni of initial viable cells per unit volume of culture to the selected concentration of the antimicrobial agent for a plurality of exposure time intervals with a time duration of each exposure time interval being expressed as determining a number of the initial viable cells in the microbial population of the test culture and a number of viable cells, expressed as N in the test culture at an end of each of the exposure time intervals t; defining f(N) to vary linearly with a normalized exposure time $n_0$ and obtaining the time rate of change A to the normalized exposure time $n_0$; and evaluating the simultaneous bactericidal and bacteriostatic of the antimicrobial agent as expressed by the rate of change A in an environment at the selected concentration. In a preferred embodiment $$f(N) = (n2)(N/N_i).$$

A method for measuring a transition activity rate, expressed as TAR representing a rate of change of activity, expressed A with a function expressed as f(CNC) of the concentration expressed as CNC, of an antimicrobial agent at a selected value of the concentration, expressed as CNC, corresponding to a discrete minimum inhibitory concentration DMIC in accordance with the invention includes determining a division time interval representing a generation time of a microbial population in an absence of any antimicrobial agent expressed as $g_0$; exposing a plurality of test cultures of the microbial population at a plurality of the concentrations CNC of the antimicrobial agent relative to the DMIC with each concentration CNC being exposed for a plurality of exposure time intervals with each time interval being expressed as t; determining an initial number N of viable cells of the microbial population per unit volume in a plurality of the test cultures, and a number of viable cells, expressed as N in the test cultures, at an end of each of the exposure time intervals t for each of the plurality of concentrations CNC; defining a function of N expressed as f(N), to vary linearly with exposure time, expressed as $n_0$ and obtaining the functions of the rate of change A with associated values of time expressed for each of the plurality of concentrations CNC; defining a function of A, expressed as g(A) representing a linear relationship between the obtained functions of the rate of change A and corresponding values of the function f(CNC); and evaluating a rate of change of g(A) with f(CNC) at the concentration CNC equal to the DMIC to obtain the transition activity rate TAR. In a preferred embodiment f(N) equals $\ln_2(N/N_i)$ and f(CNC) equals CNC or ratio of CNC/DMIC.

A method for measuring a bactericidal activity expressed as p of an antimicrobial agent in accordance with the invention includes incorporating a selected concentration of the antimicrobial agent into an agar medium; adding a number of viable microbial cells to the agar medium expressed as Ni incubating the agar medium to produce visible colonies from the Ni viable cells; counting a number of the visible colonies, expressed as Nc; and determining the bactericidal activity p from a function of Nc/Ni expressed as f(Nc/Ni). In a preferred embodiment, p equals 1/[2−(Nc/Ni)].

A method for measuring discrete minimum inhibitory concentration DMIC from a plurality of bactericidal activity determinations p over a range of concentrations expressed as CNC of an antimicrobial agent for p varying between 0.5 and 1 in accordance with the invention includes for each of the plurality of bactericidal activity determinations incorporating a selected concentration of the antimicrobial agent into a agar medium, adding Ni viable microbial cells to the agar medium, incubating the agar medium to produce visible colonies from the Ni cells, counting a number of the visible colonies of microbial cells, expressed as Nc and determining the bactericidal activity p from a function of a fraction Nc/Ni expressed as f(Nc/Ni); transforming the determined bactericidal activity p into a function of p expressed as f(p) and transforming the concentration CNC, into a function of the concentration CNC expressed as f(CNC); so as to obtain a linear relationship for data points where p decreases from 1; performing a linear regression of the transformed functions f(p) and f(CNC); and solving an equation representing the linear regression for CNC for a value of p which equals 0.5 to obtain the discrete minimum inhibitory concentration expressed as DMIC. In a preferred embodiment of the invention, p equals $1/[2-(Nc/Ni)]$ and f(p) equals $\ln_2(2p)$.

A method for measuring a minimum cidal concentration, expressed as MCC for a plurality of bactericidal activity determinations p over a range of concentration, expressed as CNC of an antimicrobial agent for p varying between 0.5 and 1 in accordance with the invention includes for each of the plurality of bactericidal determinations incorporating a selected concentration of the antimicrobial agent into an agar medium, adding Ni viable microbial cells to the agar medium, incubating the agar medium to produce visible colonies of microbial cells from the Ni cells, counting the number of expressed as NC, of the visible colonies and determining the bactericidal activity p from a function of the fraction Nc/Ni expressed as f(Nc/Ni); transforming the determined bactericidal activity p into a function of p expressed as f(p) and transforming the concentration CNC into a function of CNC expressed as f(CNC); so as to obtain a linear relationship for data points where p decreases from 1; performing a linear regression of the transformed functions f(p) and f(CNC) to produce a linear regression line; and solving an equation representing the linear regression line for CNC with p equalling 1.0 to obtain the minimum cidal concentration MCC to find dosing regimens of the antimicrobial agent which restrain growth of the microbial population. In a preferred embodiment of the invention, $$p=1/[2-(Nc/Ni)]$$

and $f(p)=\ln_2(2p)$.

A method for measuring a rate of change of bactericidal activity at a discrete minimum inhibitory concentration, expressed as DMIC expressed as a transition cidal activity rate, expressed as TCAR from a plurality of bactericidal activity determinations with each activity expressed as p over a range of concentrations, expressed as CNC of an antimicrobial agent for p varying between 0.5 and 1 in accordance with the invention includes for each of the plurality of bactericidal activity determinations incorporating a selected concentration of the antimicrobial agent into an agar medium, adding Ni viable microbial cells to the agar medium, incubating the agar medium to produce visible colonies of the microbes from the Ni cells, counting a number of the visible colonies expressed as Nc and determining the bactericidal activity p from a function of the fraction Nc/Ni expressed as f(Nc/Ni); transforming the determined bactericidal activity p into a function of p expressed as $f(p)=\ln_2(2p)$ and transforming the concentration CNC into a function of CNC, expressed as f(CNC); so as to obtain a linear relationship for data points where p decreases from 1; performing a linear regression of the transformed functions $\ln_2(2p)$ and f(CNC) to produce a linear regression line; and defining a slope of the linear regression line expressed as the quantity TCAR. In a preferred embodiment of the invention, $p=1/[2-(Nc/Ni)]$.

BEST MODE FOR CARRYING OUT THE INVENTION

1. Method for Determination of Normalized Drug Activity

Conventional procedures are used to determine the drug-free (control) generation time, $g_0$, using a portion of the culture to be exposed to the antimicrobial agent. Determination of the normalized drug activity involves removing aliquots of the growing culture, determining the number of cells per unit volume, N (CFU/ML), at the selected incubation time intervals, t, plotting a logarithmic function of N versus t, obtaining the slope of the line in the log phase of growth, i.e. where log(N) is linear with t, computing the number of generations, $n_0$, which occurred in the time interval $\Delta t$ between the starting point $N_s$ and end point $N_f$ of the log phase of growth, and computing $g_0$ as $\Delta t/n_0$. For example, if logarithms to the base 2 are used in the plot, then $n_0=\ln_2(N_f/N_s)$.

Figure 1:
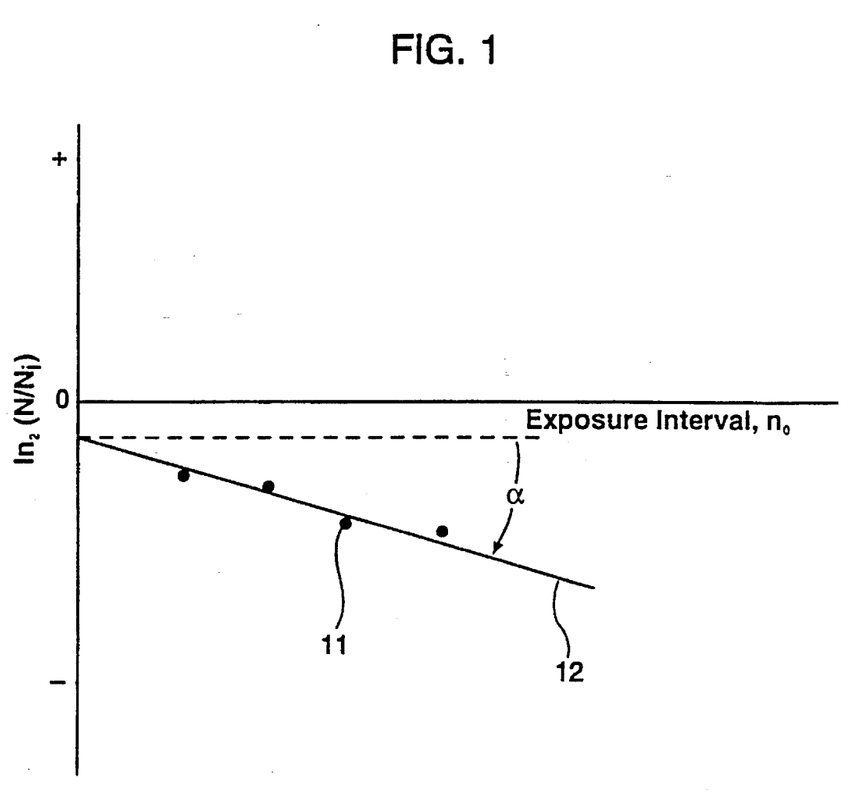
FIG. 1 is an illustration of the data and its analysis for the determination of normalized activity in accordance with the present invention.

The normalized activity, A, of the antimicrobial agent is obtained by exposing the test culture to a selected concentration of the agent, representative of the drug concentrations at the infection site. It is desirable to (1) limit the size of the initial test inoculum density $N_i$ viable cells per unit volume of culture to the selected concentration of the antimicrobial agent needed for obtaining measurable changes of N over the test interval, (2) limit the test interval to a few drug free-generations, and (3) exposing the culture to the antimicrobial agent after it has reached the beginning of the log phase of growth. The antimicrobial bacterial density, $N_i$, and the viable cell densities, N, at the end of the different exposure time intervals, t, are determined by standard methods. Each data point 11 in FIG. 1 is obtained by removing an aliquot after exposure for a time t and determining by standard methods the associated viable cell density N (CFU/ML). A linear relationship can generally be obtained between a logarithmic function of N, preferably defined as $\ln_2(N/N_i)$, and exposure times t or its equivalent representation as normalized exposure time in units of antimicrobial agent-free generations $n_0=t/g_0$.

Line 12 in FIG. 1 is the result of performing a linear regression of the data points 11, from which the value of its slope, $\tan\alpha$, is obtained. The quantity $\tan\alpha$ is the normalized activity, A, of the antimicrobial agent against the test bacterial population at the selected infection site concentration.

An alternative procedure for computing A is to perform a linear regression of the $\ln_2(N/Ni)$ data against their associated values of exposure time t (not $n_0=t/g_0$), to obtain a slope m and then to multiply m by $g_0$ to obtain A.

The normalized activity, or the Bactericidal Reduction Period (equation 3), relate laboratory test results to the simultaneous bactericidal and bacteriostatic activity of the antimicrobial agent at the selected concentration acting at the site of infection in vivo. Generally, the relationship of test results to the efficacy of the antimicrobial agent can be expected to hold even though antimicrobial agent-free generation times at the site of infection may be different from those measured in the laboratory test. Furthermore, since laboratory results are normalized with respect to the particular antimicrobial agent-free generation applicable to the test, repeatability within laboratories and reproducibility between laboratories can be expected to be significantly improved, because antimicrobial agent-free generation times are greatly affected by test conditions, such as the choice of nutrient media or incubation temperature.

Illustrative Computation of Normalized Activity

The following example is based on hypothetical data. Assume that the antimicrobial agent-free generation time has been determined as $g_0=0.5$ hours and that the initial test population density was $N_i=10^4$ CFU/ML. The measured populations at successively longer exposure intervals—in multiples of 0.25 hours, equivalent to 0.5 antimicrobial agent-free generations—are shown in the column titled N. The computation of $\ln_2(N/N_i)$ is facilitated by the relationship $\ln_2(X)=3.322 \times \log_{10}(X)$.

| t | $n_0$ | N | $\ln_2 (N/N_i)$ |
|---|---|---|---|
| 0 | 0 | $1 \times 10^4$ | 0 |
| 0.25 | 0.5 | $6.6 \times 10^3$ | −0.6 |
| 0.5 | 1.0 | $5.7 \times 10^3$ | −0.8 |
| 0.75 | 1.5 | $3.1 \times 10^3$ | −1.7 |
| 1.0 | 2.0 | $2.3 \times 10^3$ | −2.1 |
| 1.25 | 2.5 | $1.6 \times 10^3$ | −2.6 |

A linear regression of $\ln_2(N/N_i)$ against $n_0$ yields the regression line equation $\ln_2(N/N_i)=0.014-1.05\,n_0$. Since −1.05 is the slope of the regression line, it corresponds to the value of normalized activity, signifying approximately a twofold reduction in the population each antimicrobial agent-free generation time interval, or a 99.9% reduction in about 10 antimicrobial agent-free generations. If, for example, the application (infection site) antimicrobial agent-free generation time is 2 hours, rather than the 0.5 hours in the test environment, the 99.9% reduction would require an elapsed time of 10×2=20 hours.

The alternate procedure for computing A involves performing a linear regression of the $\ln_2(N/N_i)$ data against their associated values of t to obtain the regression line equation $\ln_2(N/N_i)=0.014-2.1\,n_0$. The slope is now −2.1, which when multiplied by $g_0=0.5$ also yields A=−1.05.

The method of the present invention for determining the simultaneous bactericidal and bacteriostatic activity of an antimicrobial agent by measuring a time rate of change A of a function f(N), preferably defined as $\ln_2(N/N_i)$, of the number of viable cells N in a microbial population with time of exposure to an application relevant concentration of an antimicrobial agent with the function of N expressed as f(N) being linearly related to exposure time and time expressed as the number $n_0$ of drug free division time interval $g_0$, is with reference to the preceding data explained as follows. The application relevant concentration (a selected concentration) is chosen from data provided by the manufacturer of concentrations to be achieved at the site of infection. The determination of the initial number of microbes $N_i$ in terms of (CFU/ML) is performed by standard bacterial enumeration methods, such as plating dilutions of inoculum, incubating the plates and counting the number of colonies. The number of cells N (CFU/ML) at the end of each time interval t is also determined by the above-described standard enumeration methods with the data contained in the column "N". Dividing the values of t by $g_0$ (0.5) yields the data in the column $n_0$. The linear equation defining the straight line 12 is a function of N expressed as f(N) which varies linearly with normalized exposure time $n_0$. The value A is obtained by a regression analysis of the data in the column $\ln_2(N/N_i)$ against the data in column $n_0$ as illustrated in FIG. 1. Alternately, the value A is obtained by a regression analysis of the data in the column $\ln_2(N/N_i)$ against the data in column t, followed by multiplying the slope of this regression line by $g_0$. The practical usefulness of the result A is to quantitatively evaluate the rate at which the population at the infection site will be reduced with each antimicrobial agent free generation time interval applicable to the infection site, due to bactericidal and bacteriostatic activity of the antimicrobial agent, even though the antimicrobial agent free generation time interval at the infection site may be different from $g_0$.

2. Method for Determination of Transition Activity Rates

Figure 2:
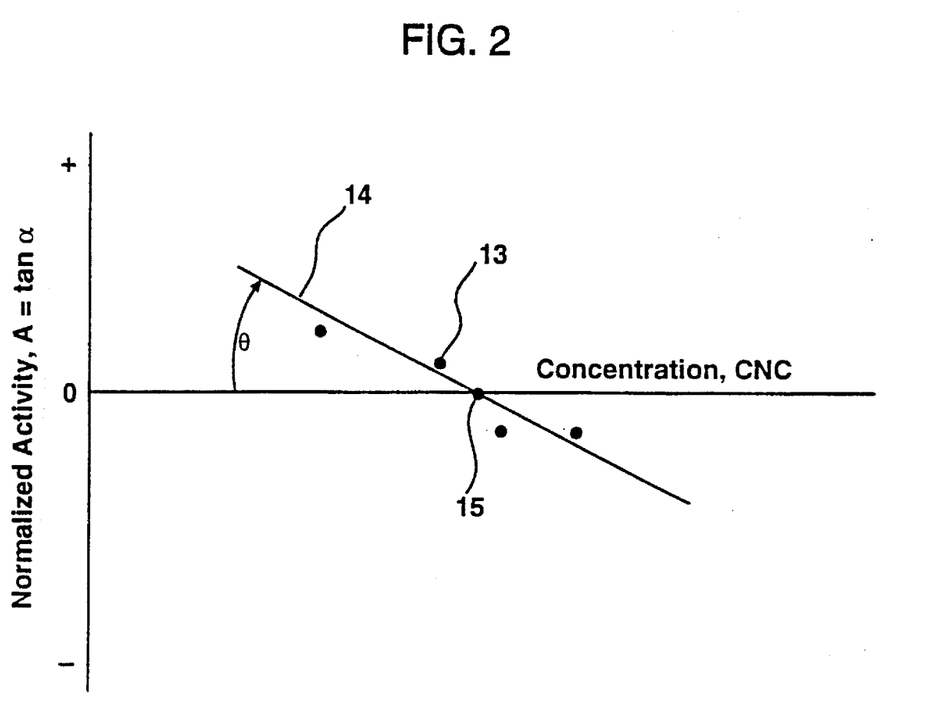
FIG. 2 is an illustration of the analysis of normalized activity data for the determination of the transition activity rate in accordance with the present invention.

The potential for eradication of a bacterial population at the application concentrations of the antimicrobial agent is measurable, quantitatively, by the rate of change of activity at the DMIC, the Transition Activity Rate, TAR. Determination of the TAR requires knowledge of the DMIC value of the antimicrobial agent against the test population. Determination of the DMIC is illustrated in FIG. 2. It involves evaluation of normalized activity as described above, but at a number of concentrations of the antimicrobial agent in the vicinity of the DMIC, preferably both below and above its expected value, which can be estimated by conventional MIC test methods, if not known from experience with the antimicrobial agent against the species being tested. In FIG. 2, data points 13 are representative of the four normalized activity values obtained at the different concentrations, CNC, of the antimicrobial agent. The linear regression line 14 in FIG. 2 is obtained from these data. The DMIC is the value of CNC where the regression line intersects the concentration axis, identified as reference numeral 15 in FIG. 2. It is computed by setting A=0 in the equation of the regression line. The tangent of the angle θ in FIG. 2 is the TAR.

The method for measuring a transition activity rate TAR representing a rate of change of activity A with a function of CNC expressed as f(CNC) of a concentration (CNC) of an antimicrobial agent at a selected value of CNC corresponding to a discrete minimum inhibitory concentration DMIC is explained with reference to FIG. 2 as follows. The antimicrobial agent free division time interval $g_0$ of the microbial population is obtained as explained above. A plurality of test cultures of the microbial population are exposed at a plurality of concentrations CNC of the antimicrobial agent related to the DMIC with each concentration CNC being exposed for a plurality of exposure intervals. An initial density $N_i$ of viable cells per unit volume of the microbial population in the plurality of test cultures and a density of viable cells N per unit volume in the test cultures at an end of each of the exposure time intervals for each of the plurality of concentrations is determined. An equivalent number of antimicrobial agent free generations $n_0$ for each of the exposure time intervals t for each of the plurality of concentrations CNC is obtained by dividing the plurality of exposure time intervals by the antimicrobial agent free generation $g_0$. A value of the time rate of change A of a density of viable cells in the test cultures from a function of N expressed as f(N) with time expressed in units of antimicrobial agent free generation $n_0$ is obtained. A function of N expressed as f(N) varying linearly with normalized exposure time $n_0$ and obtaining its rate of change A with associated values $n_0$ for each of the plurality of concentration CNC represented by data points 13 is determined as represented by linear relationship 14. The rate of change of the obtained values of A as a function of CNC is evaluated to obtain the TAR which is the tangent of the angle θ in FIG. 2 as explained above. The TAR is a measure of the potential for eradication of an offending bacterial population at infection site concentrations.

Figure 3:
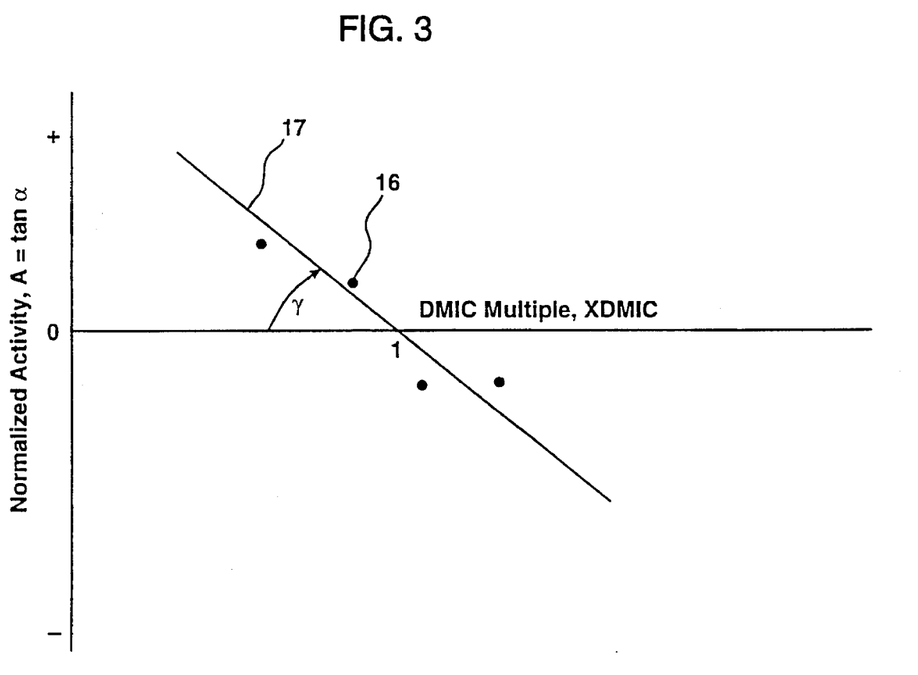
FIG. 3 illustrates the normalization of the data of FIG. 2 and its analysis for the computation of the extinction index in accordance with the present invention.

The Extinction Index is found by rearranging the data of FIG. 2 in the manner shown in FIG. 3. Specifically, it requires the expression of concentration in multiples of the DMIC, denoted as XDMIC, i.e. XDMIC=CNC/DMIC. The rearranged data is illustrated by reference numeral 16 in FIG. 3; the linear regression line of the data expressed in this fully normalized manner is represented by line 17. (Note that the regression line intersects the XDMIC axis at XDMIC=1, i.e. at the DMIC.) The tangent of the angle γ in FIG. 3 is the Extinction Index, EI. As stated above, the greater the numerical value of the TAR, the greater the potential for eradication of an offending bacterial population at concentrations above the DMIC. Because antimicrobial agent concentration has been normalized in terms of the DMIC, EI values of different antimicrobial agent acting on the same bacterial isolate can be compared to determine which drug is more likely to effectively eradicate a pathogenic population.

A method for measuring an Extinction Index EI at a selected concentration of an antimicrobial agent DMIC in accordance with the invention utilizes the same steps as discussed above in the method for measuring a transition activity rate TAR through obtaining the time rate of change of A of a number of viable cells in the test cultures from a function N and $N_i$ with time expressed in units of antimicrobial agent free generation. Thereafter, with reference to FIG. 3, a value representing DMIC as a value of CNC for which A in the function representing the obtained values of A equals zero is determined. The concentrations CNC are normalized by dividing each of the values by DMIC to obtain XDMIC. The rate of change of the obtained values A as a function of XDMIC is evaluated to obtain the extinction index EI. The extinction index EI is used to evaluate potential for the antimicrobial agent to eradicate the microbial population with potential of eradication of the microbial population increasing with an increase in the extinction index.

3. Method for Determination of Bactericidal Dose-Response Measures

The value of p, or of CA, at a selected concentration of the antimicrobial agent in the growth transition region (1>p>0.5) can be obtained by incorporating the agent into the agar medium, depositing a known number, Ni, of cells onto the surface of or into the agar, incubating the plate, counting the number of colonies, Nc, which formed on the surface of the agar and computing p from equation 4a and/or CA from equation 4b.

The utility of obtaining the value of p at a selected concentration of the antimicrobial agent is that this information can serve to also quantitate the bacteriostatic activity at these concentrations. This can be done by measuring the normalized activity A at the same concentration and solving for $g_0/g$ in equation 2a. Although limited to the range of concentrations producing restrained growth, this method provides a quantitative indications of the relative bactericidal/bacteriostatic activity of the antimicrobial agent.

A method for measuring a bactericidal activity p of an antimicrobial agent is described as follows. A selected concentration of the antimicrobial agent is incorporated into an agar medium. Ni viable microbial cells are added to the agar medium. The agar medium is incubated in a conventional manner to produce visible colonies from the Ni viable cells. The number of visible colonies Nc is counted in the conventional manner such as with a commercially available colony counter. The bactericidal activity p is determined from a function of the fraction Nc/Ni with the preferred function f(p) being equal to the quantity 1/(2−Nc/Ni).

Figure 4:
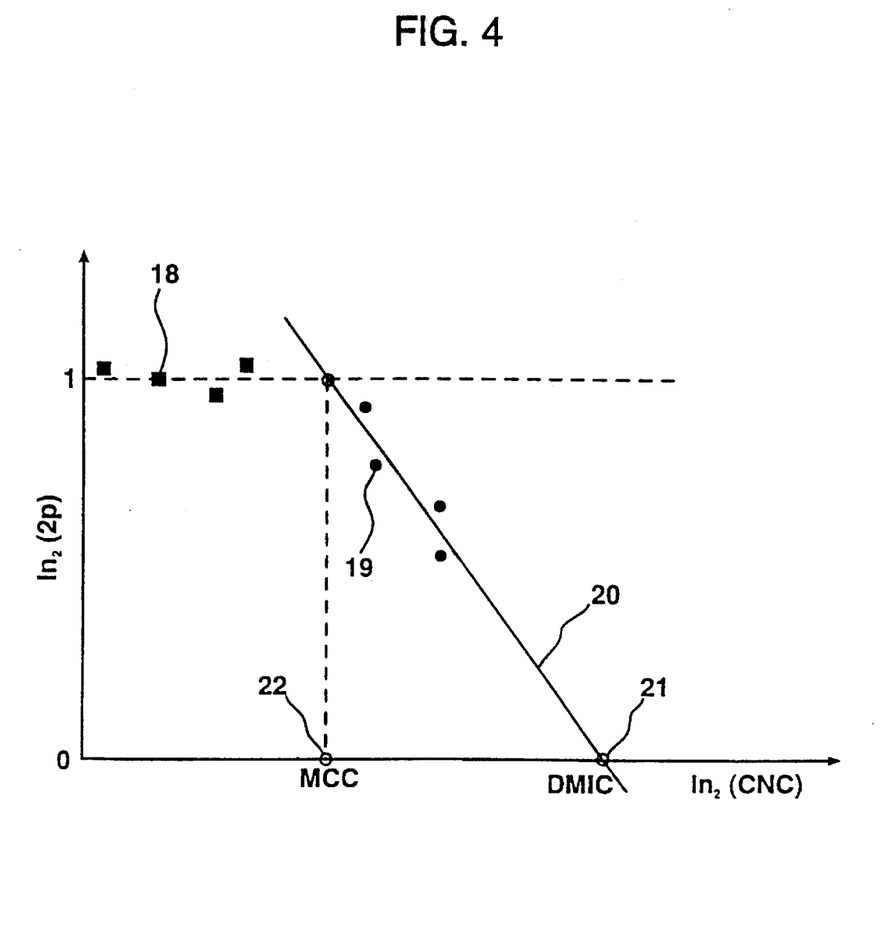
FIG. 4 illustrates the computation of bactericidal activity measures in accordance with the present invention.

The DMIC is obtained by obtaining the value of p for a number of different concentrations of the antimicrobial agent in the growth transition region, to yield a dose-response of p, or CA versus concentration. Referring to FIG. 4, the cidal activity measurements, $\ln_2(2p)$, are plotted against a suitable function of concentration, expressed as f(CNC), intended to produce a linear variation of $\ln_2(2p)$ with f(CNC). FIG. 4 is based on the assumption that a plot against $\ln_2(CNC)$ produces the desired linear dose-response. Data 19 in FIG. 4 are representative of data obtained in the desired range of concentrations and data 18 is excluded because they represent values of p close to 1 and therefore likely to be below the threshold of bactericidal activity. Line 20 in FIG. 4 is the linear regression line of the data in the desired range of concentrations; its equation has the general form $\ln_2(2p)=Y(0)+m[\ln_2(CNC)]$, where Y(0) is the vertical axis intercept of the regression line 20 and m is its slope. The DMIC, 21 in FIG. 4, is obtained by setting p=0.5 in the regression equation.

Obtaining the DMIC from colony counts on agar, rather than from total population counts in broth, has the advantage of greater reproducibility because it is less sensitive to the presence of outlier cells from the tails of the distributions of generation times or bactericidal probabilities: the progeny of such an outlier cell is accumulated into the same colony on agar—usually resulting in distinguishing size or morphology, leading to its exclusion from the count—whereas the entire progeny population is added to the population count in broth. Having a more reproducible measurement of the DMIC has the practical value of being able to reliably detect small changes in the DMIC as a basis for an early assessment of the acquisition of resistance to the antimicrobial agent after repeated exposures and reculturing.

A method for measuring discrete minimum inhibitory concentration DMIC from a plurality of bactericidal activity determinations p over a range of concentrations of an antimicrobial agent CNC for p varying between 0.5 and 1 is explained as follows. A selected concentration of the antimicrobial agent for each of the plurality of bactericidal activity determinations is incorporated into an agar medium. Ni viable microbial cells are added to the agar medium. The agar medium is incubated to produce visible colonies of microbial cells from the Ni cells. The number of visible colonies Nc is counted using conventional enumeration methods and the bactericidal activity p is determined from a function of the fraction Nc/Ni. The determined bactericidal activity p is transformed into a function f(p) and the concentration CNC is transformed into a function expressed as f(CNC) so as to obtain a linear relationship for data points 19 where p decreases from 1. A linear regression of the transformed function f(p) is performed to obtain line 20. The equation representing the linear regression for CNC is solved for a value of p which equals 0.5. The preferred function of the fraction Nc/Ni comprises $$p=1/[2-(Nc/Ni)]$$

The function f(p) equals $\ln_2(2p)$.

The Minimum Cidal Concentration (MCC), 22 in FIG. 4, is the threshold concentration of cidal activity and is obtained by setting p=1 in the regression equation. The slope of the regression line, tanβ in FIG. 4, represents the rate of change of cidal activity in the region of 1>p>0.5 and is therefore a measure of the Transition Cidal Activity Rate (TCAR).

A method for measuring a minimum cidal concentration MCC for a plurality of bactericidal activity determination p over a range of concentrations CNC of an antimicrobial agent for p varying between 0.5 and 1 is explained as follows. The steps are the same as the above-described method for measuring the discrete minimum inhibitory concentration DMIC except p is set equal to 1.

Knowledge of the MCC can serve to better define dosing regimens so as to maintain a concentration of the antimicrobial agent at the site of infection which will, as a minimum, restrain the growth of the pathogenic population.

Determination of the TCAR serves to assess the extent of static activity at the DMIC, the TSA, using equation 5 and a measurement of the combined transition activity rate, TAR. In this manner the relative bacteriostatic\bactericidal activity rates at the DMIC can be determined.

A method for measuring a rate of change of bactericidal activity at a discrete minimum inhibitory concentration DMIC expressed a transition cidal activity rate TCAR from a plurality of bactericidal activity determinations p over a range of concentrations CNC of an antimicrobial agent for p varying between 0.5 and 1 is described as follows. The steps are the same as the above-described methods for measuring the discrete minimum inhibitory concentration DMIC except that the slope of the linear regression line tan β is obtained.

The methods of this invention seek to determine the response of the dominant part—the mode—of the bacterial population to the bactericidal and bacteriostatic actions of the antimicrobial agent, seeking to minimize the effects on this response of cells from the tails of the probability distributions. But such outlier cells can be expected to be present in some practical applications. Their effect can be evaluated by paralleling the tests defined by the present invention, which call for small inoculum populations evaluated over relatively short exposure times, with tests utilizing large inoculum population—so as to increase the likelihood of outlier cells being present—with or without an increase in the exposure times to the antimicrobial agent. Differences in results will indicate the practical significance of outlier cells, if expected to be present at the site of infection.

Normalized activity, transition activity rates and bactericidal activity rates are measures of the rate of change of a dependent variable relative to an independent one, based on test measurements of both. Such rates of change are practically obtained by performing a regression of the data pairs varying approximately linearly in the region of interest. The utilization of generalized functions f(N), g(A) and F(CNC) serves to identify the need for achieving an approximately linear relationship of the data obtained from test measurements prior to performing the linear regression analysis which will yield the desired rates of change information, which is the subject matter of this invention. Linearized rate of change relationships are also used to solve for particular values of one of the variables at specified values of the other. The latter procedure, which notes the particular choice of the linearization functions, constitutes the subject matter of the invention.

An exception to the above is the function f(Nc/Ni) from which a value of the probability of successful division p is calculated at a selected concentration of the antimicrobial agent. The simplifying assumptions and analytical methodology used in the probability model lead to the particular formulation of f(Nc/Ni) given by equation 4a. Modification of these simplifying assumptions and associated mathematical treatment could lead to somewhat different forms of f(Nc/Ni). These modifications are part of the present invention provided the resulting function describes bactericidal action as defined by the model and does so largely in terms of measurements of Nc and Ni obtained from tests which allow for nearly all colonies Nc to become countable.

While the invention has been described in terms of its preferred embodiments it should be understood that numerous modifications may be made thereto without departing from the spirit and scope of the present invention. It is intended that all such modifications fall within the scope of the appended claims.

We claim:

1. A method for determining simultaneous bactericidal and bacteriostatic activity of an antimicrobial agent by measuring a time rate of change, expressed as A, of a function f(N) of a number of viable cells, expressed as N, in a microbial population per unit volume of culture with a time of exposure to a selected concentration of an antimicrobial agent with the function f(N) being linearly related to a normalized exposure time, expressed as a number $n_0$ of division time intervals $g_0$ representing a generation time of the microbial population in the absence of any antimicrobial agent comprising:

determining by measurement $g_0$ of the microbial population;

exposing a test culture of the microbial population containing a number of $N_i$ viable cells per unit volume of culture to the selected concentration of the antimicrobial agent for a plurality of exposure time intervals with a time duration of each exposure time interval being expressed as t;

determining a number $N_i$ of the initial viable cells, in the microbial population per unit volume of the test culture and a number of viable cells, expressed as N per unit volume in the test culture, at an end of each of the exposure time intervals t;

defining f(N) to vary linearly with the exposure time $n_0$ and obtaining the time rate of change A relative to the normalized exposure time $n_0$; and evaluating after determination by measurement of $g_0$ the simultaneous bactericidal and bacteriostatic activity of the antimicrobial agent as expressed by the rate of change A in an environment at the selected concentration.

2. A method in accordance with claim 1 wherein:

$$f(N) = \ln_2(N/N_i).$$

3. A method for measuring a transition activity rate, expressed as TAR, representing a rate of change of activity, expressed as A, with a function expressed as f(CNC) of the concentration, expressed as CNC, of an antimicrobial agent at a selected value of the concentration CNC corresponding to a discrete minimum inhibitory concentration expressed as DMIC comprising:

determining a division time interval of a microbial population in the absence of any antimicrobial agent expressed as $g_0$;

exposing a plurality of test cultures of the microbial population at a plurality of the concentrations CNC of the antimicrobial agent relative to the DMIC with each concentration CNC being exposed for a plurality of exposure time intervals with each time interval being expressed as t;

determining an initial number $N_i$ of viable cells of the microbial population per unit volume in a plurality of the test cultures and a number of viable cells, expressed as N per unit volume in the test cultures, at an end of each of the exposure time intervals t for each of the plurality of concentrations CNC;

defining a function of N, expressed as f(N), varying linearly with a normalized exposure time expressed as $n_0$ and obtaining functions of the rate of change A with associated values of $n_0$ for each of the plurality of concentrations CNC;

defining a function of A, expressed as g(A), representing a linear relationship between the obtained functions of the rate of change A and corresponding values of the function f(CNC); and evaluating a rate of change of g(A) with f(CNC) at the concentration CNC equal to the DMIC to obtain the transition activity rate TAR.

4. A method in accordance with claim 3 wherein:

$$f(N)=\ln_2(N/Ni).$$

5. A method in accordance with claim 3 wherein:

$$f(CNC)=CNC.$$

6. A method in accordance with claim 4 wherein:

$$f(CNC)=CNC.$$

7. A method in accordance with claim 3 wherein:
f(CNC)=XDMIC defined as a ratio of CNC/DMIC.
8. A method in accordance with claim 4 wherein:
f(CNC)=XDMIC defined as a ratio of CNC/DMIC.
9. A method for measuring a bactericidal activity, expressed as p, of an antimicrobial agent comprising:

incorporating a selected concentration of the antimicrobial agent into an agar medium;

adding a number of viable microbial cells to the agar medium expressed as Ni;

incubating the agar medium to produce visible colonies from the Ni viable cells;

counting a number of the visible colonies expressed as Nc; and determining solely the bactericidal activity p from a function of Nc/Ni expressed as f(Nc/Ni).

10. A method in accordance with claim 9 wherein:

$$p=1/[2-(Nc/Ni)].$$

11. A method for measuring a discrete minimum inhibitory concentration, expressed as DMIC, from a plurality of bactericidal activities, with each bactericidal activity being expressed as p, over a range of concentrations, expressed as CNC, of an antimicrobial agent for p varying between 0.5 and 1 comprising:

for each of the plurality of bactericidal activity determinations incorporating a selected concentration of the antimicrobial agent into an agar medium, adding Ni viable microbial cells to the agar medium, incubating the agar medium to produce visible colonies from the Ni cells, counting a number of the visible colonies of microbial cells expressed as Nc and determining the bactericidal activity p from a function of a fraction Nc/Ni expressed as f(Nc/Ni);

transforming the determined bactericidal activity p into a function of p expressed as f(p) and transforming the concentration CNC into a function of the concentration CNC, expressed as f(CNC), so as to obtain a linear relationship for data points where p decreases from 1;

performing a linear regression of the transformed functions f(p) and f(CNC); and solving an equation representing the linear regression for CNC for a value of p which equals 0.5 to obtain the discrete minimum inhibitory concentration expressed as DMIC.

12. A method in accordance with claim 11 wherein:

$$p=1/[2-(Nc/Ni)].$$

13. A method in accordance with claim 11 wherein:

$$f(p)=\ln_2(2p).$$

14. A method in accordance with claim 12 wherein:

$$f(p)=\ln_2(2p).$$

15. A method for measuring a minimum cidal concentration, expressed as MCC, from a plurality of bactericidal activity determinations each expressed as p, over a range of concentrations, expressed as CNC, of an antimicrobial agent for p varying between 0.5 and 1 comprising:

for each of the plurality of bactericidal activity determinations incorporating a selected concentration of the antimicrobial agent into an agar medium, adding Ni viable microbial cells to the agar medium, incubating the agar medium to produce visible colonies of microbial cells from the Ni cells, counting a number, expressed as NC, of the visible colonies and determining the bactericidal activity p from a function of the fraction Nc/Ni expressed as f(Nc/Ni);

transforming the determined bactericidal activity p into a function of p expressed as f(p) and transforming the concentration CNC into a function of CNC, expressed as f(CNC), so as to obtain a linear relationship for data points where p decreases from 1;

performing a linear regression of the transformed functions f(p) and f(CNC) to produce a linear regression line; and solving an equation representing the linear regression line for CNC with p equalling 1.0 to obtain the minimum cidal concentration, expressed as MCC.

16. A method in accordance with claim 15 wherein:

$$p=1/[2-(Nc/Ni)].$$

17. A method in accordance with claim 15 wherein:

$$f(p)=\ln_2(2p).$$

18. A method in accordance with claim 16 wherein:

$f(p)=ln_2(2p)$.

19. A method for measuring a rate of change of bactericidal activity at a discrete minimum inhibitory concentration, expressed as DMIC, expressed as a transition cidal activity rate, expressed as TCAR, from a plurality of bactericidal activity determinations with each activity expressed as p, over a range of concentrations, expressed as CNC, of an antimicrobial agent for p varying between 0.5 and 1 comprising:

for each of the plurality of bactericidal activity determinations incorporating a selected concentration of the antimicrobial agent into an agar medium, adding Ni viable microbial cells to the agar medium, incubating the agar medium to produce visible colonies of microbes from the Ni cells, counting a number of the visible colonies expressed as Nc and determining the bactericidal activity p from a function of the fraction Nc/Ni expressed as f(Nc/Ni);

transforming the determined bactericidal activity p into a function of p, expressed as $ln_2(2p)$ and transforming the concentration CNC into a function of CNC, expressed as f(CNC), so as to obtain a linear relationship for data points where p decreases from 1;

performing a linear regression of the transformed functions $ln_2(2p)$ and f(CNC) to produce a linear regression line; and determining a slope of the linear regression line expressed as the quantity TCAR.

20. A method in accordance with claim 19 wherein:

$p=1/[2-(Nc/Ni)]$.

* * * * *